(12) United States Patent
Waltersdorff et al.

(10) Patent No.: US 8,425,526 B2
(45) Date of Patent: Apr. 23, 2013

(54) ADJUSTABLE IMPACTOR

(75) Inventors: William L. Waltersdorff, Hernando, MS (US); Charles Wayne Allen, Southaven, MS (US); Kevin W. Belew, Hernando, MS (US); Michael Scott McCaig, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 878 days.

(21) Appl. No.: 11/873,927

(22) Filed: Oct. 17, 2007

(65) Prior Publication Data

US 2008/0109006 A1    May 8, 2008

Related U.S. Application Data

(60) Provisional application No. 60/829,748, filed on Oct. 17, 2006.

(51) Int. Cl.
*A61B 17/92* (2006.01)
*A61B 17/56* (2006.01)

(52) U.S. Cl.
USPC .................... 606/99; 606/91; 16/900

(58) Field of Classification Search .......... 16/110.1, 16/430, 900; 30/167.1; 33/495–500; 403/53–54, 403/84; 606/80–81, 90–91, 99–100
See application file for complete search history.

(56) References Cited

U.S. PATENT DOCUMENTS

| | | | | |
|---|---|---|---|---|
| 1,810,715 A | * | 6/1931 | Larson et al. | 74/546 |
| 2,187,852 A | * | 1/1940 | Friddle | 606/100 |
| 5,284,483 A | * | 2/1994 | Johnson et al. | 606/86 R |
| 5,320,625 A | * | 6/1994 | Bertin | 606/91 |
| 5,474,560 A | * | 12/1995 | Rohr, Jr. | 606/91 |
| 6,478,500 B1 | * | 11/2002 | Farenholtz | 403/84 |
| 6,767,153 B1 | * | 7/2004 | Holbrook | 403/56 |
| 2003/0050645 A1 | | 3/2003 | Parker et al. | |
| 2003/0158559 A1 | * | 8/2003 | Diaz | 606/91 |
| 2004/0153063 A1 | | 8/2004 | Harris | |
| 2005/0085823 A1 | * | 4/2005 | Murphy | 606/91 |
| 2005/0149043 A1 | | 7/2005 | Parry et al. | |
| 2005/0177172 A1 | * | 8/2005 | Acker et al. | 606/99 |
| 2005/0209604 A1 | * | 9/2005 | Penenberg et al. | 606/91 |
| 2005/0216022 A1 | | 9/2005 | Lechot et al. | |
| 2005/0228395 A1 | | 10/2005 | Auxepaules et al. | |
| 2006/0229630 A1 | * | 10/2006 | Collins et al. | 606/91 |
| 2007/0293869 A1 | | 12/2007 | Conte et al. | |
| 2008/0021481 A1 | | 1/2008 | Burgi | |

FOREIGN PATENT DOCUMENTS

| | | |
|---|---|---|
| EP | 1832248 | 9/2007 |
| WO | WO-2009136284 | 11/2009 |

\* cited by examiner

*Primary Examiner* — Kevin T Truong
*Assistant Examiner* — Larry E Waggle, Jr.
(74) *Attorney, Agent, or Firm* — Ropes & Gray LLP

(57) ABSTRACT

An adjustable impactor for a tool comprises a handle, a first link, and a second link. The first link is pivotably attached to the handle. The second link is pivotably attached to the first link. The second link has a connector configured to attach to the tool. A method for impacting an orthopaedic component inside a surgical cavity includes a step for pivoting a first link relative to a handle. Another step pivots a second link relative to the first link. The first and second links are locked. A step attaches a tool to the second link. An impacting step impacts the handle such that the handle transmits the force from the impact through the first and second links to the tool.

28 Claims, 5 Drawing Sheets

ADJUSTABLE IMPACTOR

CROSS-REFERENCE TO RELATED APPLICATIONS

This application claims priority to U.S. Provisional Application 60/829,748 filed Oct. 17, 2006.

BACKGROUND OF THE INVENTION

1. Field of the Invention

The present invention relates generally to hip arthroplasty and, more particularly, instruments used in hip arthroplasty.

2. Related Art

Total hip arthroplasties are typically done using a variety of approaches. Generally, the approach chosen is because of how the surgeons were taught. Every approach has its advantages or disadvantages. Typically, there are at least two different shape cup impactors utilized to do acetabular cup impactions: those impactors that are straight and those that have some sort of bend or curve in them. Thus, the state of the art requires at least two separate instruments to be supplied for total hip arthroplasties. It would be an advantage if one instrument could be used in either approach.

SUMMARY

An embodiment of the invention comprises an adjustable impactor for a tool comprising a handle, a first link and a second link. The first link is pivotably attached to the handle. The second link is pivotably attached to the first link. The second link has a connector configured to attach to the tool.

An embodiment may further comprise a pommel surface attached to the handle. the pommel surface is configured to receive a force and transmit the force to the handle. Another embodiment may further comprise a first locking member configured to lock the first link to the handle. Another embodiment may further comprise the second link further comprises a second locking member configured to lock the second link to the first link.

In another embodiment, the first and second locking members further comprise a bias member. The bias member is configured to bias the first and second links into a locked position. The bias member may be a spring. The first and second links may be configured to have a plurality of locked positions. The connector may be pivotably attached to the second link or a threaded member.

Another embodiment further comprises a plurality of first links. The plurality of first links and second link may further comprise a stop configured to limit the amount of rotation of the links relative to adjacent links.

Another embodiment comprises a method for impacting an orthopaedic component inside a surgical cavity. The method includes a step for pivoting a first link relative to a handle. Another step pivots a second link relative to the first link. The first and second links are locked. A step attaches a tool to the second link. An impacting step impacts the handle such that the handle transmits the force from the impact through the first and second links to the tool.

Another embodiment further comprises the step of biasing the first link to the handle. Another step comprises the step of biasing the second link to the first link. The locking steps may further comprise locking the links in one of a plurality of locking positions. Alternatively, another embodiment further comprises the step of stopping the pivoting of the links at a maximum pivot relative to the adjacent link. Another embodiment may include the step of threadably connecting the tool to the second link.

This invention puts the choice in the surgeon's hands for the particular style of impactor desired. The surgeon can set the instrument to meet the surgical demand and desired approach. The adjustable impactor can be set straight, with an offset, or with a curve in the general shape. This eliminates the need for separate instruments, which saves space in sterilization trays and ultimately is a cost savings for all parties.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings.

DETAILED DESCRIPTION OF THE EMBODIMENTS

The following description of the preferred embodiment(s) is merely exemplary in nature and is in no way intended to limit the invention, its application, or uses.

Figure 1:
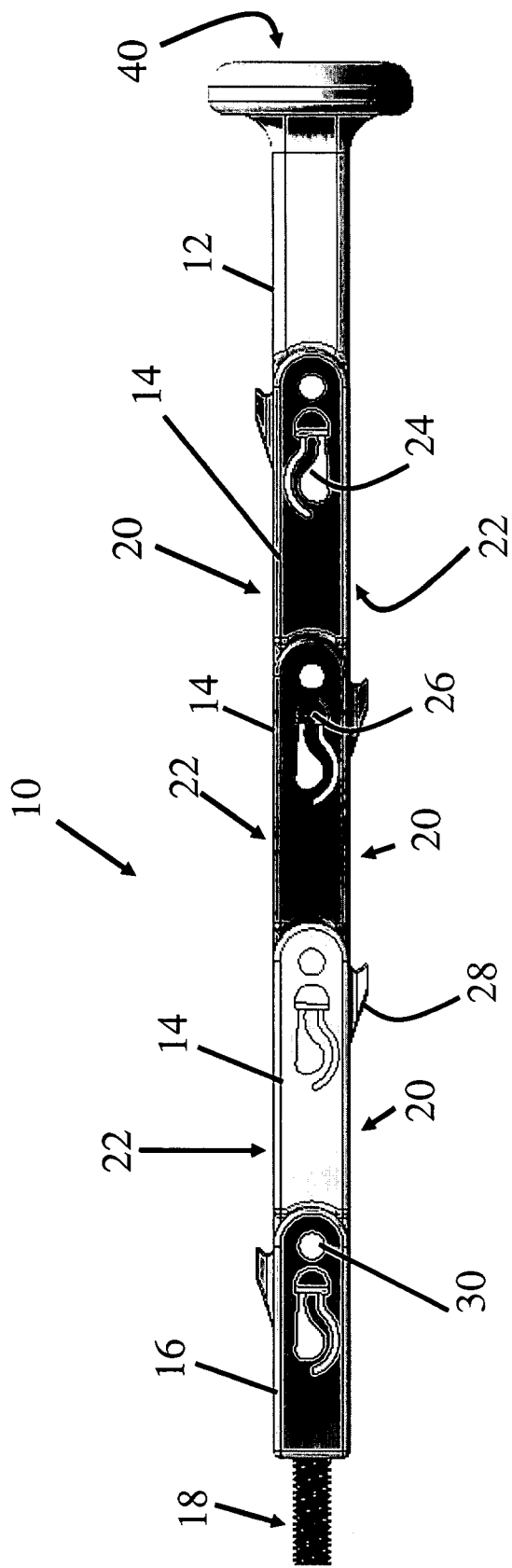
FIG. 1 is a side view of a first embodiment of an adjustable impactor in a first orientation.
Figure 2:
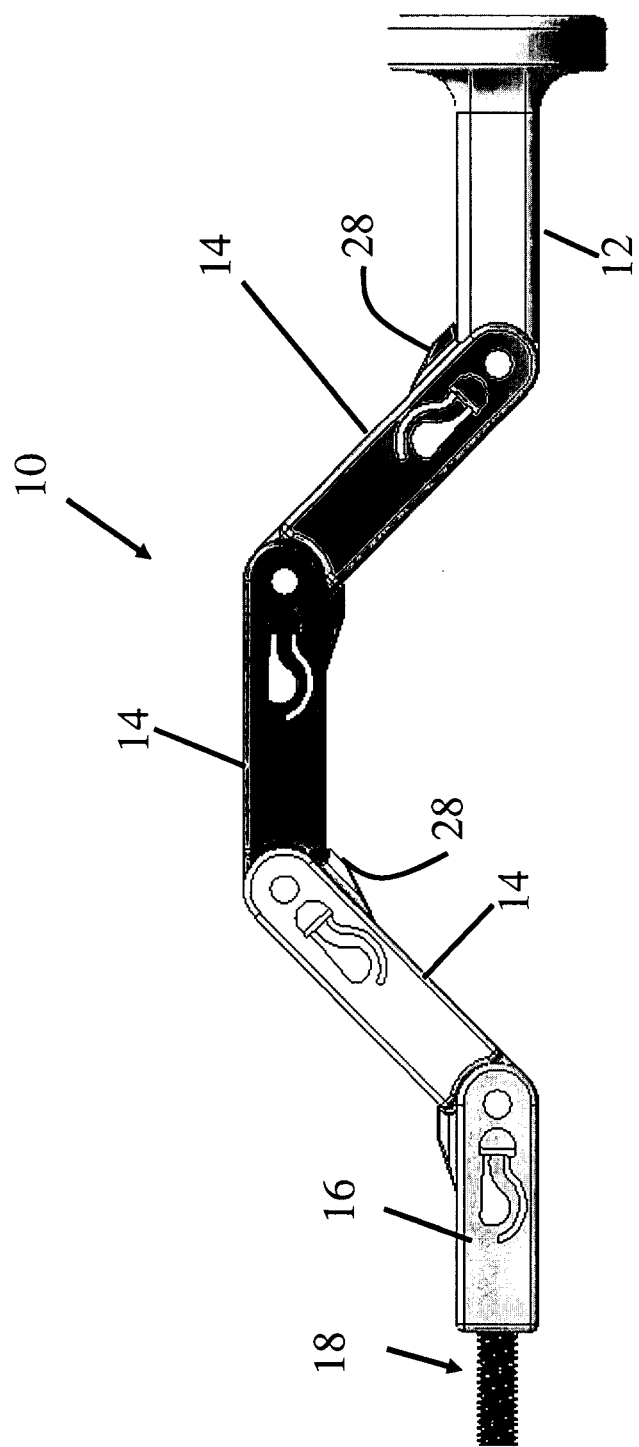
FIG. 2 is a side view of the first embodiment shown in FIG. 1 in a second orientation.

FIGS. 1 and 2 illustrate a first embodiment of an adjustable impactor 10. The adjustable impactor 10 includes a handle 12, at least one first link 14, and a second link 16. In the embodiment depicted in FIGS. 1 and 2, the adjustable impactor 10 has three first links 14, with two links having a first orientation and one link having a second orientation. Those of ordinary skill in the art would understand that a greater or lesser number of links 14, 16 may be used. The second link 16 includes a connector 18. The connector 18 is used to connect a tool, such as an impactor head, to the adjustable impactor 10. In the embodiment depicted in FIG. 1, the connector 18 is a threaded fastener but those of ordinary skill in the art would understand that other mechanisms for connection may be used.

The first link 14 has a first surface 20 and a second surface 22. Each link 14, 16 has a spring 24 and a locking pin 26. A user pulls back on the locking pin 26 against the spring 24 to adjust the adjustable impactor 10. The spring 24 may be a separate component or it may be integral with the link. For example, the spring 24 may be machined using a laser cutter or electrical discharge machining Each link 14, 16 may include a stop 28. The stop 28 prevents over-travel of the link 14, 16 when the adjustable impactor 10 is adjusted. The handle 12 and the links 14, 16 are connected through the use of pivot pins 30.

The handle 12 includes a pommel surface 40. The pommel surface 40 is configured to receive a blow from a tool. The links 14, 16 transmit the force from the blow through the impactor handle 10 to the tool connected to the connector 18. By adjusting the links 12, 14, the impactor handle may be configured to transmit the force nonlinearly from the pommel surface 40 to the tool 18 and avoid interference from anatomical features.

The impactor handle 10 may be used to impact an orthopaedic device such as a femoral hip stem implant or an acetabular cup. The impactor handle 10 would be placed from inside a surgical cavity to outside the body. The impactor handle 10 would be attached to a tool which would overlie the orthopaedic device. The links 14, 16 would be pivoted to avoid interference with any anatomical structure inside the surgical cavity. The links would be locked in place, and the handle 12 of the impactor handle 10 would be impacted, for example, by a mallet. The locked links transmit the force from the handle 12 outside the body to the tool overlying the orthopaedic device.

Figure 3:
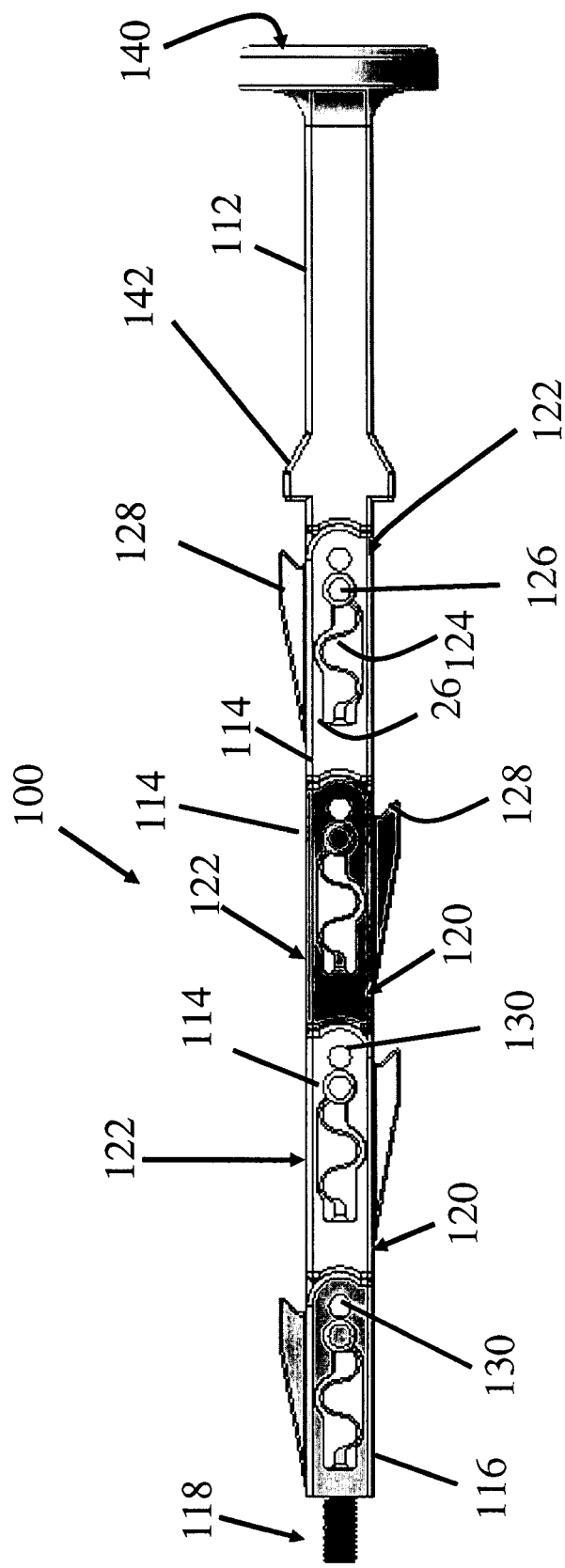
FIG. 3 is a side view of a second embodiment of an adjustable impactor in a first orientation.
Figure 4:
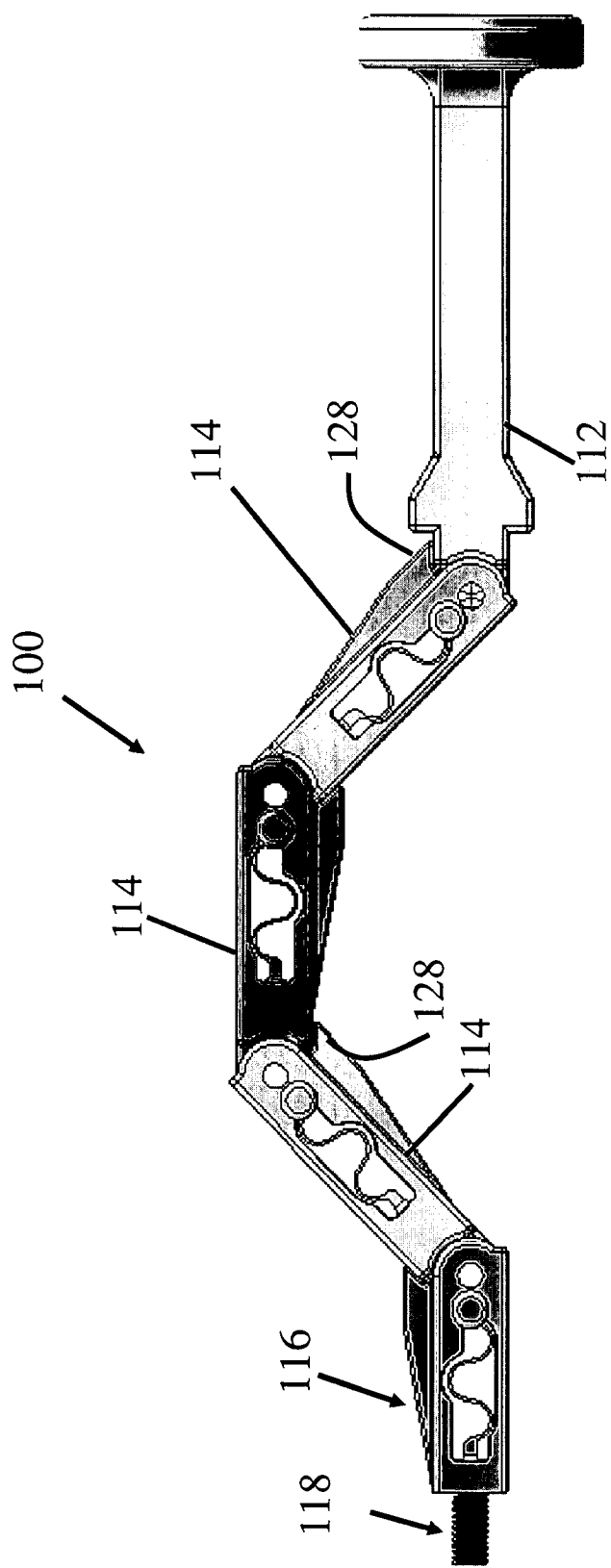
FIG. 4 is a side view of the second embodiment shown in FIG. 3 in a second orientation.

FIGS. 3 and 4 illustrate a second embodiment of an adjustable impactor 100. The adjustable impactor 100 includes a handle 112, at least one first link 114, and a second link 116. In the embodiment depicted in FIGS. 3 and 4, the adjustable impactor 100 has three first links 114, with two links having a first orientation and one link having a second orientation. Those of ordinary skill in the art would understand that a greater or lesser number of links 114, 116 may be used. The second link 116 includes a connector 118. The connector 118 is used to connect a tool, such as an impactor head, to the adjustable impactor 100.

In the embodiment depicted in FIG. 3, the connector 118 is a threaded fastener but those of ordinary skill in the art would understand that other mechanisms for connection may be used. The first link 114 has a first surface 120 and a second surface 122. Each link 114, 116 has a spring 124 and a locking pin 126. A user pulls back on the locking pin 126 against the spring 124 to adjust the adjustable impactor 100. The spring 124 may be a separate component or it may be integral with the link. For example, the spring 124 may be machined using a laser cutter or electrical discharge machining. Each link 114, 116 may include a stop 128. The stop 128 prevents over-travel of the link 114, 116 when the adjustable impactor 100 is adjusted. The handle 112 and the links 114, 116 are connected through the use of pivot pins 130. The handle 112 includes a pommel surface 140 and a flared portion 142. The flared portion 142 may protect a surgeon's hand from traveling down the handle 100.

Figure 5:
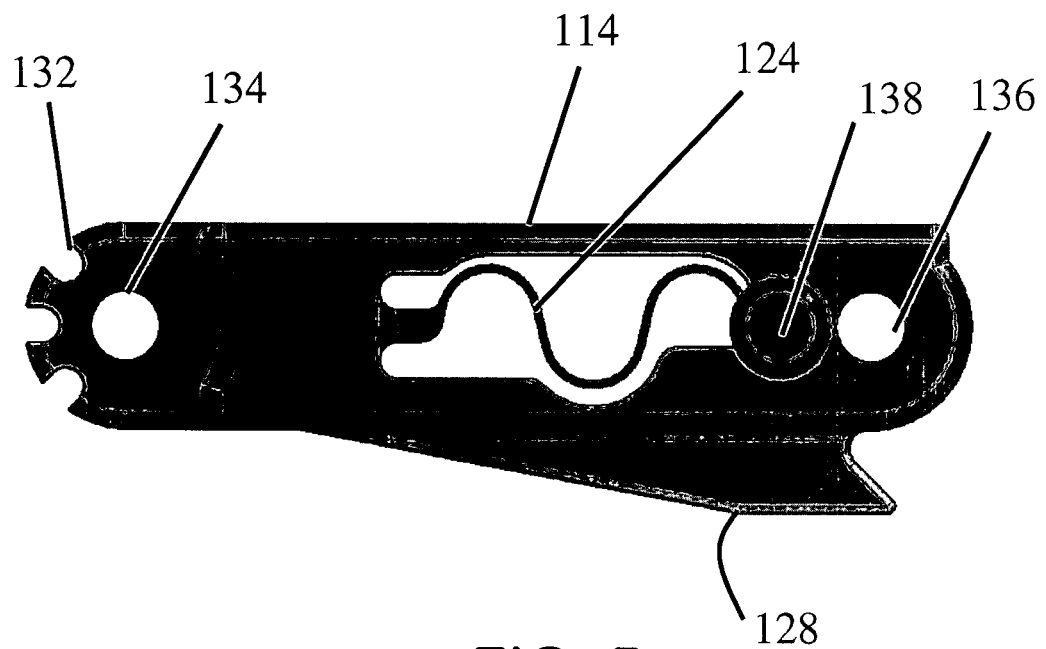
FIG. 5 is a side view of a first link.
Figure 6:
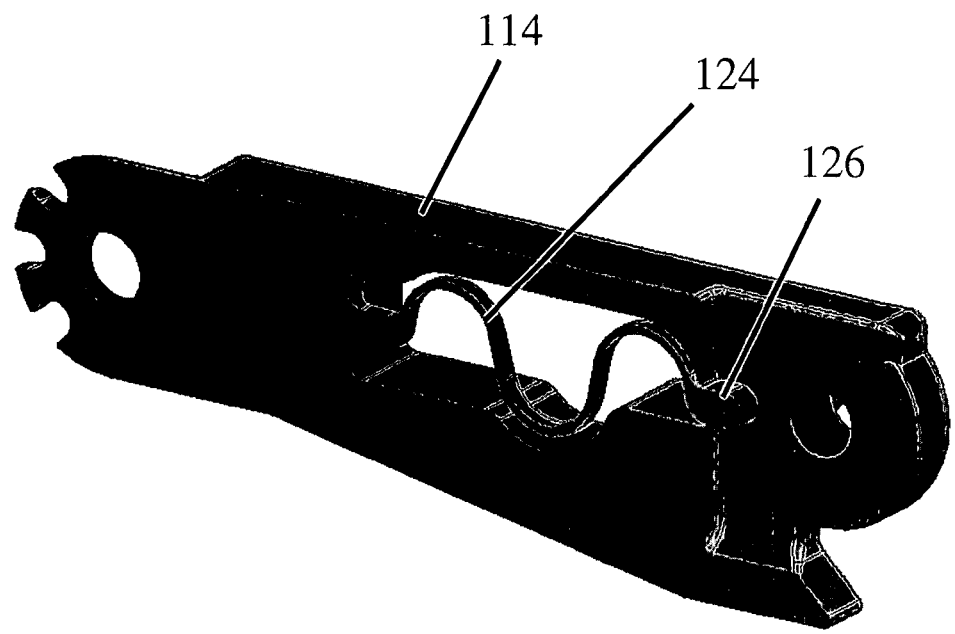
FIG. 6 is a sectional perspective view of the first link shown in FIG. 5.

FIGS. 5 and 6 illustrate the first link 114 in greater detail. As noted above, the first link 114 includes the spring 124 and the stop 128. The first link 114 also includes the locking pin 126. In the embodiment depicted in FIGS. 5 and 6, the locking pin 126 is integrally formed as a portion of the spring 124, and knobs 138 are affixed to each side of the pin 126, such as by welding. In other embodiments, the locking pin 126 is a separate component that is directionally biased by the spring 124. The first link also includes at least one detent 132, a first hole 134, and a second hole 136. The holes 134, 136 are shaped and dimensioned to receive the pivot pin 130. The detent 132 is shaped and dimensioned to receive a portion of the pin 126. Thus, when the adjustable impactor 100 is assembled, the locking pin 126 engages one of the detents 132 to maintain an orientation of the assembly.

To adjust the adjustable impactor 100, a user pulls back on the pin 126 until it disengages from the detent 132 and rotates the link 114, 116. The spring force of the spring 124 may be selected to balance the function of biasing the pin 126 towards the detent 132 against the ability of a plurality of users to overcome the spring force in order to adjust the adjustable impactor 100. If the spring force is too high, the pin 126 will positively engage the detent 132, but many users will be unable to overcome the spring force to achieve adjustment. If the spring force is too low, many users will have the ability to adjust the adjustable impactor 100, but the locking pin 126 may become unintentionally disengaged from the detent 132. Therefore, a compromise in spring force must be reached.

Those of ordinary skill in the art would understand that although internal springs 24, 124 are shown, external springs could equally be used. Further, those of ordinary skill in the art would understand that the handle 12, 112 may be a separate component attached to the link 14, 114 through the use of a fastener. Finally, those of ordinary skill in the art would understand that the instrument could be utilized for a stem and broach impactor as well.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An adjustable impactor for a tool having a first orientation and a second orientation, comprising:
   an elongated handle having a handle longitudinal axis;
   an elongated handle link having a handle link longitudinal axis;
   an elongated tool connection link having a tool connection link longitudinal axis and having a connector configured to attach to the tool, and
   at least one elongated intermediate link comprising an intermediate link longitudinal axis, the at least one elongated intermediate link positioned between the elongated handle link and the elongated tool connection link;
   wherein each of the elongated handle link, the elongated tool connection link, and the at least one elongated intermediate link comprises a constraining mechanism configured to limit angulation between two of the links to a selected one of a predetermined number of angles, and to lock the two links relative to each other at the selected angle;
   wherein when in the first orientation, the handle link longitudinal axis, the tool connection link longitudinal axis, and the intermediate link longitudinal axis are substantially parallel, and
   when in the second orientation, at least a portion of the handle link longitudinal axis and the tool connection link longitudinal axis are not substantially parallel, and
   whereby, when the elongated handle is impacted, at least a component of the impact is transmitted along the tool connection link longitudinal axis.

2. The adjustable impactor of claim 1, wherein the handle longitudinal axis, the handle link longitudinal axis and the tool connection link longitudinal axis are coplanar when in the first and second orientations.

3. The adjustable impactor of claim 1, wherein the links are connected to each other using hinge joints.

4. The adjustable impactor of claim 1, wherein the constraining members include a plurality of detents or a biasing mechanism.

5. The adjustable impactor of claim 4, wherein the biasing mechanisms include an interpositional member that is configured to be interposed in one of the detents to form a locking relationship.

6. The adjustable impactor of claim 5, wherein the biasing mechanism includes a spring.

7. The adjustable impactor of claim 6, wherein the elongated handle link and the elongated tool connection link have a plurality of discrete locked positions.

8. The adjustable impactor of claim 1, wherein the connector is pivotably attached to the elongated tool connection link.

9. The adjustable impactor of claim 8, wherein the connector is a threaded member.

10. The adjustable impactor of claim 1, wherein at least one of the elongated handle link, the at least one elongated intermediate link, and the elongated tool connection link further comprises a stop configured to limit rotation of that link relative to an adjacent link.

11. The adjustable impactor of claim 1, wherein each of the elongated handle link, the at least one elongated intermediate link, and the elongated tool connection link further comprises a connection structure, wherein each of the connection structures is recessed at one end of the link to allow the elongated links to lie substantially flush with respect to each other.

12. The adjustable impactor of claim 1, wherein the links are connected to each other using hinge connections.

13. The adjustable impactor of claim 12, wherein a first of the hinge connections connects the elongated handle and the elongated handle link, wherein a second of the hinge connections connects the elongated handle link and one of the at least one elongated intermediate links, and wherein a third of the hinge connections connects one of the at least one elongated intermediate links and the elongated tool connection link, and wherein each of the elongated links between two adjacent hinge connections is straight along an entire length of the elongated link.

14. The adjustable impactor of claim 12, wherein a first of the hinge connections connects the elongated handle and the elongated handle link, wherein a second of the hinge connections connects the elongated handle link and the at least one elongated intermediate link, and wherein a third of the hinge connections connects the at least one elongated intermediate link and the elongated tool connection link, and wherein a line connecting any two adjacent hinge connections defines a longitudinal axis of the associated elongated link.

15. The adjustable impactor of claim 1, wherein the elongated handle link and the at least one elongated intermediate link are substantially identical to one another.

16. An adjustable impactor for a tool comprising:
an elongated handle link comprising a first link longitudinal axis, a connection opening, and a detent end including a plurality of detents or a biasing end that comprises an interpositional member that is biased toward the biasing end using a biasing member;
an elongated tool connection link comprising a tool connection link longitudinal axis, a connection opening, and a detent end including a plurality of detents or a biasing end that comprises an interpositional member that is biased toward the biasing end using a biasing member;
at least one elongated intermediate link comprising an intermediate link longitudinal axis, a detent end, and a biasing end, each of the detent end and the biasing end including a connection opening configured to form a pivot connection with a connection opening of another link, and wherein the detent end comprises a plurality of detents and the biasing end comprises an interpositional member that is biased toward the biasing end using a biasing member;
wherein the detent end of each link is configured to receive an interpositional member of another link and thereby be constrained in one of a number of predetermined angles relative to the other link to form a rigid construct that includes the elongated handle link, the elongated tool connection link, and the at least one elongated intermediate link such that when a handle of the rigid construct is impacted, at least a portion of the impact is transmitted along the tool connection link longitudinal axis.

17. The adjustable impactor of claim 16, wherein the adjustable impactor has a first orientation and a second orientation and wherein when in the first orientation, the handle link longitudinal axis, the tool connection link longitudinal axis, and the intermediate link longitudinal axis are substantially parallel, and
when in the second orientation, at least a portion of the handle link longitudinal axis and the tool connection link longitudinal axis are not substantially parallel.

18. The adjustable impactor of claim 17, wherein the handle link longitudinal axis, the tool connection link longitudinal axis and the intermediate link longitudinal axis are coplanar when in the first and second orientations.

19. The adjustable impactor of claim 16, wherein the tool connection link is engaged with an acetabular cup.

20. The adjustable impactor of claim 16, wherein the tool connection link is engaged with a femoral hip stem implant.

21. The adjustable impactor of claim 16, further comprising an elongated handle comprising a pommel surface extending from an end of the elongated handle.

22. The adjustable impactor of claim 16, further comprising a stop that limits rotation of the elongated handle link relative to another link.

23. The adjustable impactor of claim 16, wherein the connector is a threaded member.

24. An assembly for impacting an orthopaedic device into a patient's anatomy, comprising:
an adjustable impactor comprising:
an elongated handle having a handle longitudinal axis;
an elongated handle link having a handle link longitudinal axis;
at least one elongated intermediate link having an intermediate link longitudinal axis;
at least one tool connection link having a tool connection link longitudinal axis and having a connector,
wherein the elongated handle link comprises a constraining mechanism configured to limit angulation between the elongated handle link and the elongated handle to a selected one of a predetermined number of angles, and to lock the elongated handle link and the elongated handle relative to each other at the selected angle,
wherein the at least one elongated intermediate link comprises a constraining mechanism configured to limit angulation between the elongated handle link and the at least one elongated intermediate link to a selected one of a predetermined number of angles, and to lock the elongated handle link and the at least one intermediate link relative to each other at the selected angle, and
wherein the at least one tool connection link comprises a constraining mechanism configured to limit angulation between the at least one tool connection link and the at least one elongated intermediate link to a selected one of a predetermined number of angles, and to lock the at least one tool connection link and the at least one elongated intermediate link relative to each other at the selected angle;

wherein when the links are locked relative to one another and the elongated handle is impacted, at least a component of the impact is transmitted along the tool connection longitudinal axis to the connector;

wherein when in the first orientation, the handle link longitudinal axis, the intermediate link longitudinal axis, and the tool connection link longitudinal axis are locked in a straight orientation such that the adjustable impactor has a single longitudinal axis, and when in the second orientation, at least a portion of the handle link longitudinal axis and the tool connection link longitudinal axis are locked with respect to one another so that the impactor does not have a single longitudinal axis.

25. The assembly of claim 24, wherein the connector is engaged with an orthopaedic device.

26. The assembly of claim 25, wherein the orthopaedic device is a femoral hip stem implant.

27. The assembly of claim 25, wherein the orthopaedic device is an acetabular cup.

28. The assembly of claim 24, wherein the adjustable impactor further comprises a pommel surface extending from the elongated handle.

* * * * *